US012564510B2

(12) United States Patent
Garcia Rojas et al.

(10) Patent No.: US 12,564,510 B2
(45) Date of Patent: Mar. 3, 2026

(54) NASAL DILATOR APPARATUS

(71) Applicants: Alejandro Garcia Rojas, Winters, CA (US); Valerie Fournier, Winters, CA (US)

(72) Inventors: Alejandro Garcia Rojas, Winters, CA (US); Valerie Fournier, Winters, CA (US)

(73) Assignee: MODERN MAMMOTH TECHNOLOGIES, LLC, Jasper, GA (US)

( * ) Notice: Subject to any disclaimer, the term of this patent is extended or adjusted under 35 U.S.C. 154(b) by 561 days.

(21) Appl. No.: 17/586,748

(22) Filed: Jan. 27, 2022

(65) Prior Publication Data

US 2022/0160533 A1 May 26, 2022

Related U.S. Application Data

(63) Continuation of application No. PCT/US2020/047437, filed on Aug. 21, 2020.

(60) Provisional application No. 62/890,961, filed on Aug. 23, 2019.

(51) Int. Cl.
A61F 5/08 (2006.01)

(52) U.S. Cl.
CPC ..................................... A61F 5/08 (2013.01)

(58) Field of Classification Search
CPC ......... A61M 2210/01618; A61M 29/00; A61F 5/56; A61F 5/08
USPC ........................................................ 606/199
See application file for complete search history.

(56) References Cited

U.S. PATENT DOCUMENTS

| | | | | |
|---|---|---|---|---|
| 1,255,578 | A * | 2/1918 | Boxley | A61F 5/08 606/199 |
| 1,481,581 | A * | 1/1924 | Woodward | A61F 5/08 606/199 |
| 5,895,409 | A | 4/1999 | Mehdizadeh | |
| 5,922,006 | A * | 7/1999 | Sugerman | A61F 5/08 606/204.45 |
| 6,270,512 | B1 | 8/2001 | Rittmann | |
| D572,361 | S | 7/2008 | Noce | |
| D575,397 | S | 8/2008 | Noce | |
| 8,182,504 | B2 | 5/2012 | Yazdi | |

(Continued)

FOREIGN PATENT DOCUMENTS

| | | |
|---|---|---|
| CN | 105999522 A | 8/2016 |
| DE | 102005037843 | 2/2007 |

(Continued)

OTHER PUBLICATIONS

European Patent Office (EPO), Communication (Extended European Search Report) issued Jul. 14, 2023, related European Application No. 20856070.6, pp. 1-11, claims searched, pp. 12-15.

(Continued)

*Primary Examiner* — Jocelin C Tanner
(74) *Attorney, Agent, or Firm* — O'BANION & RITCHEY LLP; John P. O'Banion

(57) ABSTRACT

A "frame-like" nasal dilator that is configured to open a user's nasal passages and maintain the user's nasal passages in an open position to improve breathing. The nasal dilator has an overall shape that mimics the shape of a butterfly, with right and left stent sections or "wings" that apply gentle pressure to open the nasal passages.

16 Claims, 4 Drawing Sheets

(56)  References Cited

U.S. PATENT DOCUMENTS

| | | | |
|---|---|---|---|
| D713,031 S | 9/2014 | Mccormick | |
| D726,312 S | 4/2015 | Johnson | |
| D737,965 S | 9/2015 | Bende | |
| 10,219,934 B2 | 3/2019 | Wang | |
| 10,426,652 B2 | 10/2019 | O'Connell | |
| 2006/0260613 A1* | 11/2006 | Pinter | A61M 15/08 |
| | | | 128/206.11 |
| 2009/0277459 A1 | 11/2009 | Al-Zeir | |
| 2010/0063532 A1 | 3/2010 | Moore | |
| 2014/0246023 A1 | 9/2014 | Maryanka | |
| 2014/0326244 A1 | 11/2014 | Orts Paya | |
| 2015/0196420 A1 | 7/2015 | Ede | |
| 2017/0119571 A1* | 5/2017 | Pepper | A61M 21/02 |

FOREIGN PATENT DOCUMENTS

| | | |
|---|---|---|
| FR | 1341906 | 11/1963 |
| WO | 0117468 A1 | 3/2001 |
| WO | 2021041228 | 3/2021 |

OTHER PUBLICATIONS

ISA/US, United States Patent and Trademark Office (USPTO), International Search Report and Written Opinion issued Nov. 10, 2020, related PCT international application No. PCT/US2020/047437, pp. 1-9, with claims searched, pp. 10-14.

Houghton Mifflin Harcourt, "The American Heritage dictionary of the English Language", p. 1101, definition of "merge", 5th edition, 2011, 3 pages.

European Patent Office (EPO), official action issued Jul. 14, 2025, related European Application No. 20856070.6, pp. 1-6; claims examined, pp. 7-10.

* cited by examiner

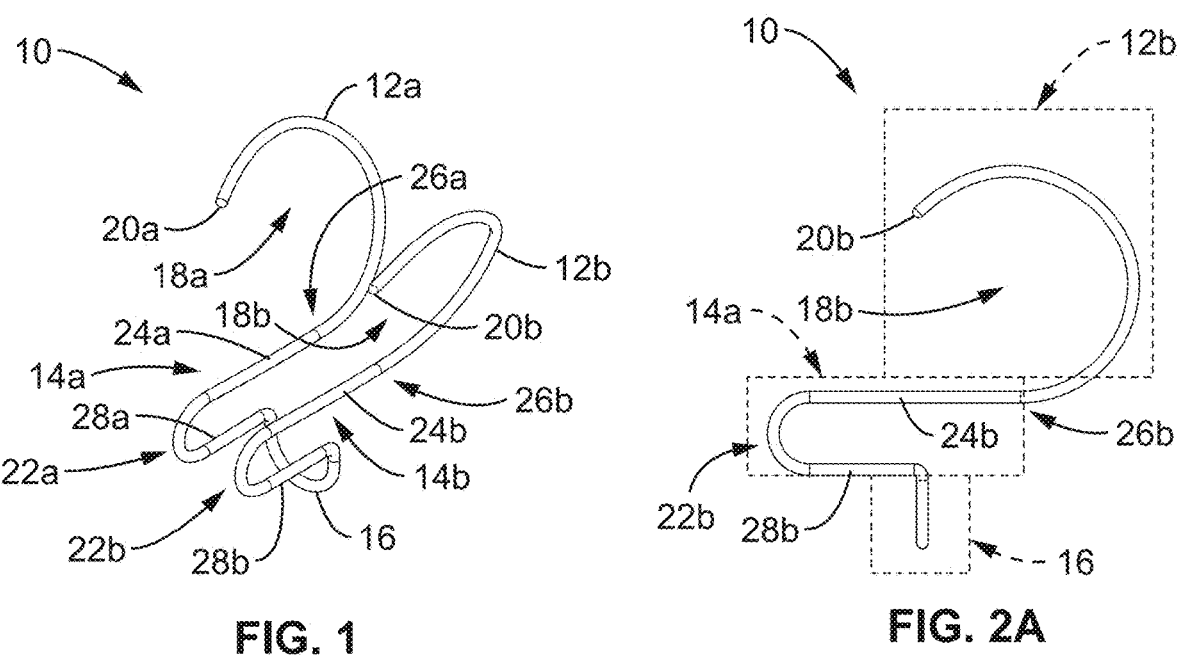
FIG. 1
FIG. 2A
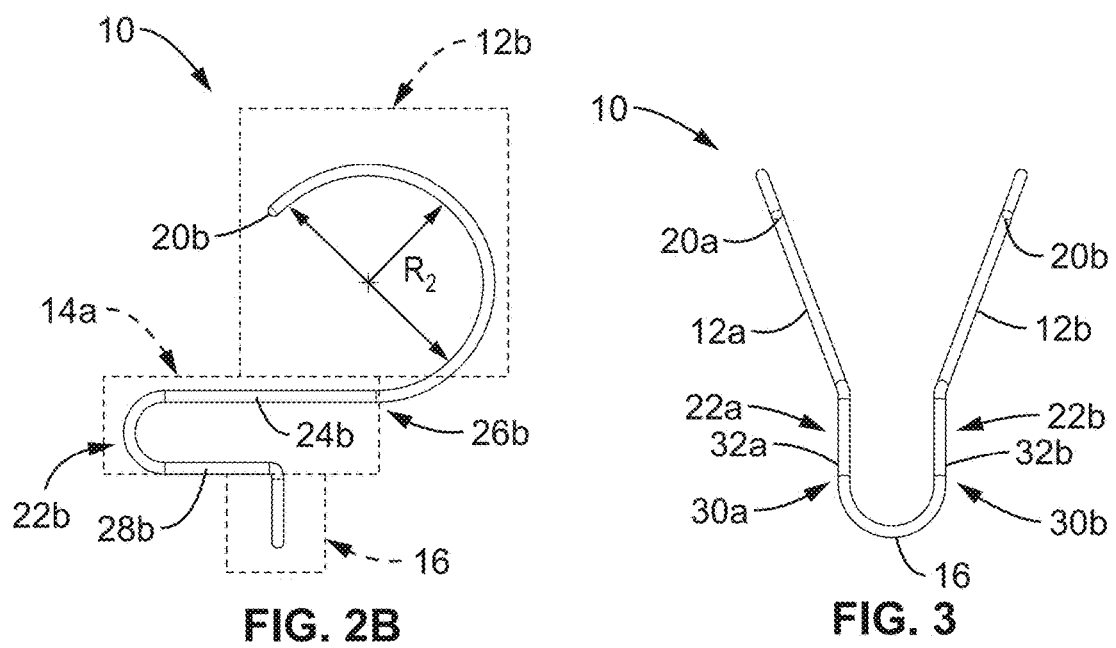
FIG. 2B
FIG. 3

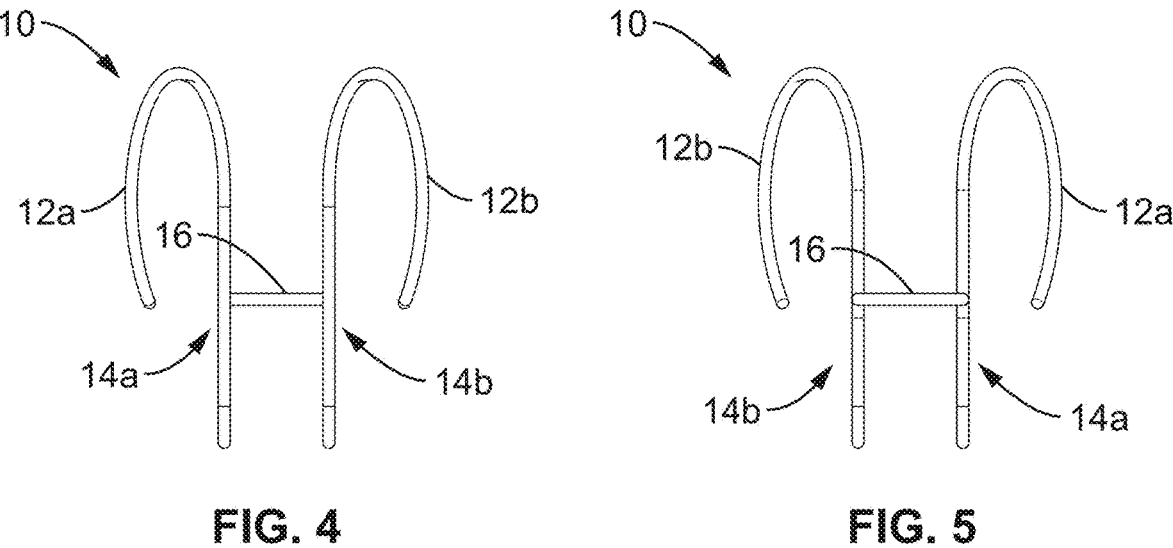
FIG. 4          FIG. 5
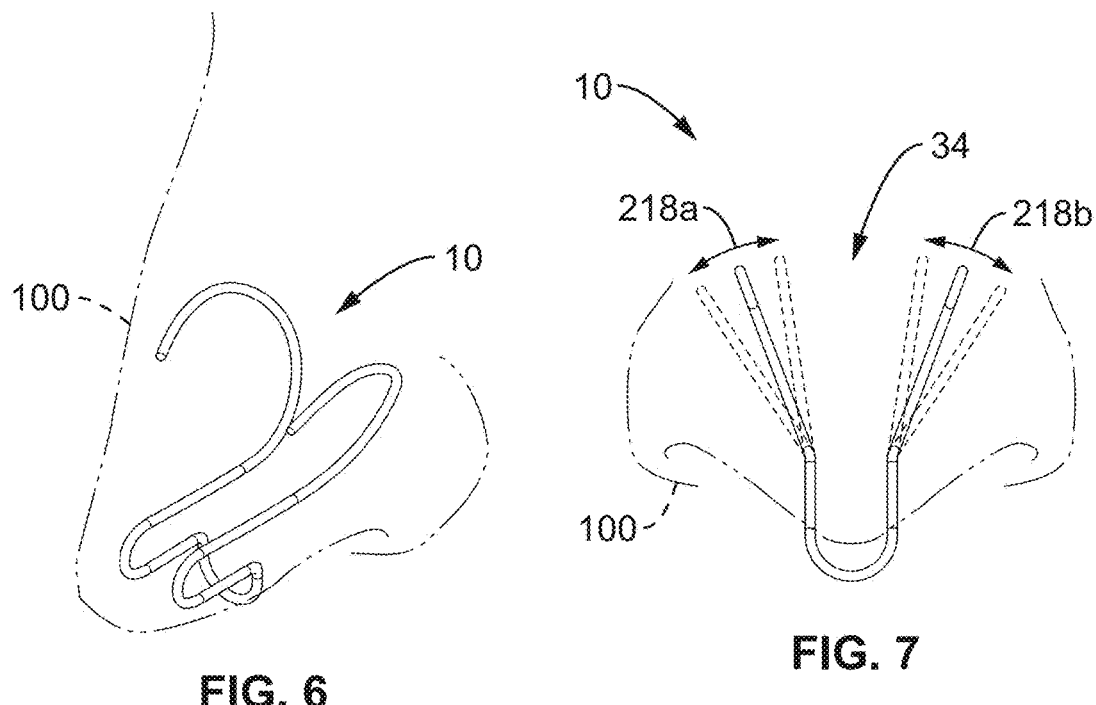
FIG. 6
FIG. 7

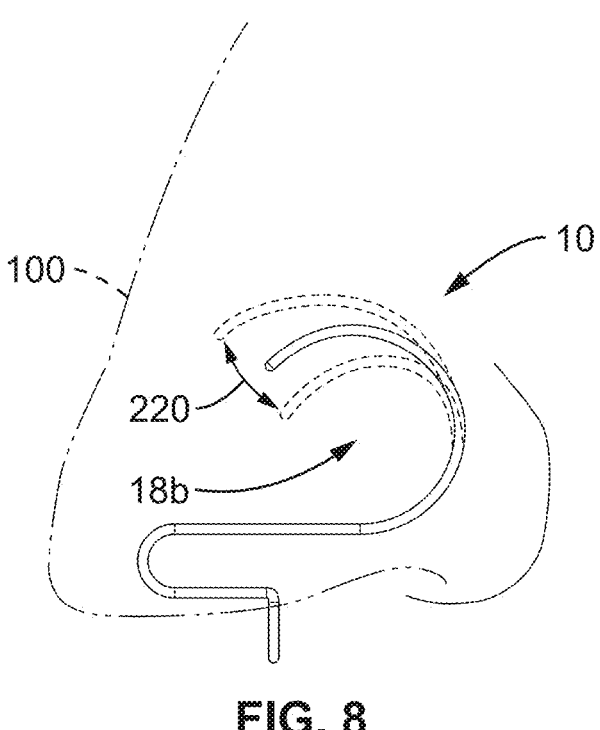
FIG. 8
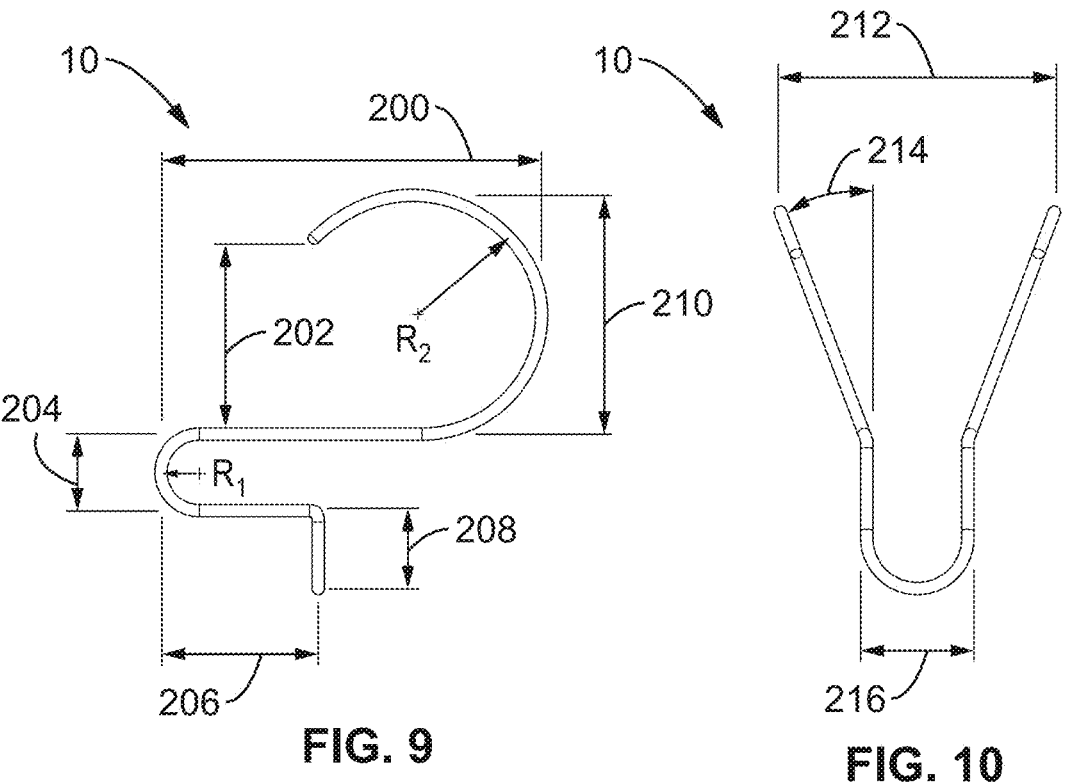
FIG. 9            FIG. 10

NASAL DILATOR APPARATUS

CROSS-REFERENCE TO RELATED APPLICATIONS

This application claims priority to, and is a 35 U.S.C. § 111(a) continuation of, PCT international application number PCT/US2020/047437 filed on Aug. 21, 2020, incorporated herein by reference in its entirety, which claims priority to, and the benefit of, U.S. provisional patent application Ser. No. 62/890,961 filed on Aug. 23, 2019, incorporated herein by reference in its entirety. Priority is claimed to each of the foregoing applications.

STATEMENT REGARDING FEDERALLY SPONSORED RESEARCH OR DEVELOPMENT

Not Applicable

The above-referenced PCT international application was published as PCT International Publication No. WO 2021/041228 A1 on Mar. 4, 2021, which publication is incorporated herein by reference in its entirety.

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to nasal dilators, and more particularly to a nasal dilator apparatus configured to be worn inside a person's nasal cavity.

2. Background Discussion

Many individuals suffer from conditions such as a deviated septum or allergies that restrict the flow of air through their nasal passages, As a result, breathing through the nose becomes difficult and inconvenient. Some individuals who experience this difficulty compensate by breathing through their mouth which, when sustained over a long period of time, can cause lung irritation from inhaling foreign particles that would otherwise be filtered by breathing through the nose. Additionally, restricted nasal passages can lead to snoring and sleep disturbances. Therefore, there is a need for an apparatus that can open an otherwise restricted nasal passage and which is easy and convenient to wear.

BRIEF SUMMARY

This disclosure describes a nasal dilator apparatus that is configured to open a user's nasal passages and maintain the user's nasal passages in an open position to improve breathing.

In one embodiment, the nasal dilator apparatus comprises a bilaterally symmetrical "frame-like" structure formed from a flexible material with sufficient stiffness to retain its shape but provide sufficient flexibility to be inserted into the nasal passages and adjust to the interior size and shape of the passages. For illustrative purposes, the apparatus comprises a right section, a left section, and a bridge section connecting the right and left sections in laterally spaced apart positions. The apparatus has an overall shape that mimics the shape of a butterfly, with the right and left sections or "wings" applying gentle pressure to open the nasal passages.

Insertion of the nasal dilator apparatus into user's nostrils opens occluded nasal passages and prevents occlusion during breathing. The nasal dilator apparatus provides an alternative to surgery for individuals who suffer from a condition that makes breathing through the nose difficult, such as in the case of a deviated septum or swelling due to allergies or other conditions.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 1 is a perspective view of an embodiment of a nasal dilator apparatus according to the present disclosure.

FIG. 2A is right side view of the nasal dilator apparatus of FIG. 1, the left side being a mirror image thereof.

FIG. 2B is right side view of the nasal dilator apparatus of FIG. 1 and FIG. 2A, with the center of the piriform arcuate section and radial extent shown, the left side being a mirror image thereof.

FIG. 3 is a front view of the nasal dilator apparatus of FIG. 1.

FIG. 4 is a top view of the nasal dilator apparatus of FIG. 1.

FIG. 5 is a bottom view of the nasal dilator apparatus of FIG. 1.

FIG. 6 is a perspective view of the nasal dilator apparatus of FIG. 1 shown positioned in a person's nose depicted in phantom lines for context.

FIG. 7 is a front view of the nasal dilator apparatus of FIG. 6 showing how the "flare" of the stents can be adjusted to accommodate a particular user with different lateral positions depicted by the dashed lines.

FIG. 8 is a side view of the nasal dilator apparatus of FIG. 6 showing how the curvature of a stent can be adjusted to accommodate a particular user with different curvatures depicted by the dashed lines.

FIG. 9 is a side view of the nasal dilator apparatus of FIG. 1 showing areas of variable dimensions.

FIG. 10 is a front view of the nasal dilator apparatus of FIG. 1 showing areas of variable dimensions.

DETAILED DESCRIPTION

Figure 11:
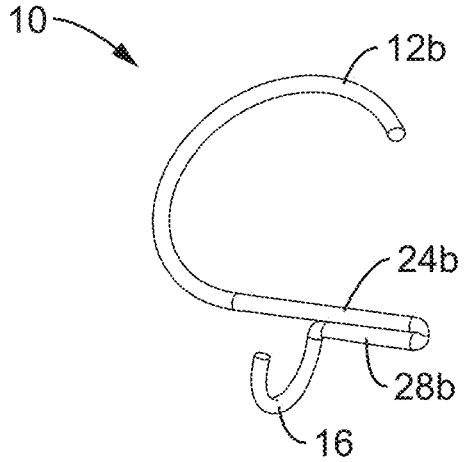
FIG. 11 is a partial side view of an embodiment of the nasal dilator apparatus as seen from the left side, illustrating minimal spacing between upper and lower support segments.

By way of example, and not of limitation, this disclosure describes a nasal dilator apparatus configured to be worn inside a person's nasal cavity. In one embodiment, the "intranasal" dilator apparatus described herein rests anterior to the nasal concha within what is commonly referred to as the inside of the nose. It will be appreciated that the interior of the human nose is symmetrical and hence the nasal dilator apparatus has a corresponding symmetry.

Referring now to FIG. 1 through FIG. 5, in one embodiment the nasal dilator apparatus 10 comprises (a) a pair of intranasal stents 12a, 12b, (b) a pair of support sections 14a, 14b, and (c) a bridge section 16.

Each of the stents 12a, 12b is arcuate in shape and is configured to be inserted into, and rest within, the posterior portion of the nasal cavity (e.g., inside the nostrils). More specifically, in one embodiment each stent 12a, 12b is defined by a corresponding main/posterior curve 18a, 18b that terminates at a corresponding distal end 20a, 20b. The curvature is preferably semicircular to circular in shape such that the stent can extend in a posterosuperior direction and approximately follow the curve of the inferior edge of the piriform aperture of the nose. The most lateral portion of the curve applies pressure to the piriform aperture. In one embodiment, each stent has a C-shape as illustrated in FIG. 2A and FIG. 2B. FIG. 2A and FIG. 2B show a right side view of the nasal dilator apparatus of FIG. 1, and FIG. 2B denotes the center of the piriform arcuate section and radial extent with a radius of curvature $R_2$.

Each of the support sections 14a, 14b has a corresponding arcuate anterior portion 22a, 22b that fits into the cone of the nose to provide support for a corresponding stent. Accordingly, the support sections anchor the stents and prevent them from falling downward. More specifically, in one embodiment each support section 14a, 14b comprises a corresponding anterior curved portion 22a, 22b that extends into (a) a corresponding substantially straight upper segment 24a, 24b that in turn merges into a corresponding stent 12a, 12b at a corresponding location 26a, 26b proximal to the stent, and (b) a corresponding substantially straight lower segment 28a, 28b that in turn merges into a corresponding side 30a, 30b of the bridge section 16.

Two sides 30a, 30b of the bridge section 16 connect ("bridge") the support sections 14a, 14b such that they are held in a substantially parallel spaced apart configuration. As a result, the stents 12a, 12b are also held in a spaced part configuration. However, as can be seen from FIG. 1 and FIG. 3, in one embodiment the stents 12a, 12b are not held in a parallel configuration but diverge laterally.

The bridge section 16 is also positioned distal to the anterior portions 22a 22b of the corresponding support sections 14a, 14b. In one embodiment, the bridge section 16 is arcuate and configured to fit against and straddle the columella of the nose which covers the nasal septum. This is the only portion of the nasal dilator apparatus that is visible when it is being worn. The visible portion is not limited to functionality and may be/include any number of decorative materials or designs. In one embodiment, the bridge section may include substantially straight segments 32a, 32a on each side that merge into the corresponding lower segments of the support sections.

Referring also to FIG. 6 through FIG. 8 for context, when the nasal dilator apparatus 10 is placed inside the nose 100, from a profile/side view, the arcuate anterior portion of each support section mimics the anatomical structure of, and rests within, the cone of the greater alar cartilage (inside the tip of the nose). As described above, this configuration anchors the apparatus in the nose. The combination of the arcuate shape, cranial direction, and flared spacing of the stents creates pressure on the nasal valve and dilates the nasal passages.

When properly adjusted by the individual user for their anatomy the nasal dilator apparatus will enlarge the nasal valve area by the diameter of the nasal passages, and thereby increase airflow through the nasal valve area without applying pressure to the lesser alar cartilage. For example, FIG. 7 illustrates how the divergent spacing or "flare" 34 of the stents can be adjusted to accommodate a particular user. The angle of this flare can be adjusted based upon user preference to better fit their individual anatomy as illustrated by the positions of the dashed lines. FIG. 8 shows how the curvature of a stent can be adjusted to accommodate a particular user as illustrated by the positions of the dashed lines.

When in place, the apparatus mimics the profile of a butterfly, with the stents being "wings" that apply gentle pressure to open the nasal passages. The support sections mimic the body portion of a butterfly with the body portion supporting the wings.

It will be appreciated that the interior of a human nose can vary in shape and size. Therefore, the nasal dilator apparatus described herein typically would not be a "one size fits all" type of device. The size, shape, angles, and curvatures of the stents, support sections and bridge section can be varied to accommodate a large array of nose anatomies.

FIG. 7 through FIG. 12 illustrate areas of possible variability in size, shape, angle, curvature and positioning. By way of example, and not of limitation, ranges of variability for those areas are listed below.

200=from about 12 mm to about 25 mm.
202=from about 0 mm to about 100 mm.
204=from about 3 mm to about 5 mm.
206=from about 4 mm to about 15 mm.
208=from about 5 mm to about 10 mm.
210=from about 8 mm to about 20 mm.
212=from about 15 mm to about 25 mm typically, and up to about 50 mm if angle 214 is about 90 degrees where the stents are flat or horizontal.
214=from about 0 degrees to about 90 degrees, where 0 degrees is vertical and 90 degrees is where the stents are flat or horizontal, and typically about 15 degrees from vertical.
216=from about 5 mm to about 10 mm.
218a, 218b=possible variability for repositioning the stents after the user sets the initial position, such as about a 5 degree to about a 10 degree adjustment throughout the day for comfort and function.
220=from about 2 mm to about 5 mm.
R1=from about 0 mm to about 1.5 mm, where an R1 of 0 mm indicates that there is no spacing between an upper segment (24a, 24b) and corresponding lower segment (28a, 28b) as illustrated in FIG. 11.
R2=from about 4 mm to about 7.5 mm.

Again, the foregoing are examples only and indicate the wide degree of variability available for manufacturing different sizes of the apparatus, fitting the apparatus to a user's anatomy, and/or allowing the user to make adjustments.

Figure 12:
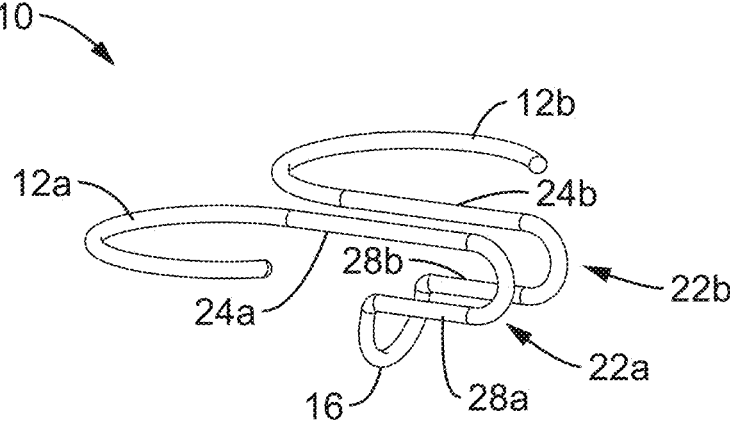
FIG. 12 is a perspective view of an embodiment of the nasal dilator apparatus illustrating the stents in a flat (horizontal) position.

Note that, even if angle 214 is extended to about 90 degrees wherein the stents are substantially flat or horizontal as illustrated in FIG. 12, the nasal dilator apparatus will remain in place by applying pressure to the inner side of the nasal orifices.

It will be appreciated that the nasal dilator apparatus described in this disclosure may be formed in various ways and from various materials known to those skilled in the art. For example, the stents, base sections, and bridge section can be one or more separate structures that are connected together. Another example is that each connection between a stent and a support section, and each connection between a support section and the bridge section, may be an integrated seamless connection such that a unitary structure is formed. The apparatus may comprise a single resilient wire that is formed into the stents, support sections, and bridge section.

Examples of materials that can be used to form the apparatus include, but are not limited to, coated metals and plastic materials. Preferably the material is malleable under certain forces to allow the individual user to make minor adjustments and customize it for their use. This also allows the apparatus to deform upon unexpected external forces. For example, the apparatus may be fabricated from a flexible metal alloy material that form the stents, support sections, and bridge section. The metal alloys may comprise, for example, stainless steel, nickel-titanium or titanium-molybdenum. All or a portion of the apparatus may be covered with a biocompatible material such as a polymer. Or, the apparatus itself may comprise a biocompatible material, such as a polymer, that is formed into the stents, support sections, and bridge section.

The apparatus may be formed, for example, from a flexible and bendable cylindrical shaped material having, for example, a diameter in the range from about 1.2 mm to about 0.5 mm, that can be bent into shape at the factory and adjusted by the user. In one embodiment, the material comprises FDA approved silicone coated stainless steel wire.

It will be appreciated that various terms have been used in this disclosure to assist the reader with understanding the structure, function and use of the nasal dilator apparatus. For example, the term "anterior" is used to refer to the front of the nose or nasal cavity, the term "posterior" is used to refer to the rear of the nasal cavity, the term "proximal" is used to refer to front, and the term "distal" is used to refer to rear. Those terms, as well as others used herein, are used according to their ordinary meanings.

From the description herein, it will be appreciated that the present disclosure encompasses multiple embodiments which include, but are not limited to, the following:

1. A nasal dilator apparatus, comprising: first and second intranasal stents; first and second support sections; and an arcuate bridge section; wherein each support section comprises an arcuate anterior portion, a substantially straight upper segment extending from the arcuate anterior portion and merging into a corresponding stent, and a substantially straight lower segment extending from the arcuate anterior portion and merging into a corresponding side of the bridge section; wherein the bridge section symmetrically bridges the first and second support sections in a spaced apart lateral position and wherein the stents are spaced apart; and wherein the bridge section is positioned distal to the anterior portions of the support sections.

2. The apparatus of any preceding or following embodiment: wherein each stent is connected to a corresponding support section; wherein each support section is connected to a corresponding side of the bridge section; and wherein each connection between a stent and a support section, and each connection between a support section and the bridge section, is an integrated seamless connection.

3. The apparatus of any preceding or following embodiment, wherein the apparatus comprises a flexible metal alloy material.

4. The apparatus of any preceding or following embodiment, wherein the flexible metal alloy material comprises stainless steel, nickel-titanium or titanium-molybdenum.

5. The apparatus of any preceding or following embodiment, wherein at least a portion of the apparatus is covered with a biocompatible material.

6. The apparatus of any preceding or following embodiment, wherein the biocompatible material comprises a polymer.

7. The apparatus of any preceding or following embodiment, wherein the apparatus comprises a single resilient wire formed into the stents, support sections, and bridge section.

8. The apparatus of any preceding or following embodiment, wherein the apparatus comprises a biocompatible material formed into the stents, support sections, and bridge section.

9. The apparatus of any preceding or following embodiment, wherein the biocompatible material comprises a polymer.

10. The apparatus of any preceding or following embodiment, wherein each stent has an arcuate shape.

11. The apparatus of any preceding or following embodiment, wherein each stent and associated support section in combination has a wing-like shape.

12. The apparatus of any preceding or following embodiment, wherein the stents have a posteriorly divergent lateral spacing.

13. A nasal dilator apparatus, comprising: a first arcuate intranasal stent; a second arcuate intranasal stent; a first support section; a second support section; and an arcuate bridge section having a first side and a second side; wherein the first support section comprises an arcuate anterior portion, a substantially straight upper segment extending from the arcuate anterior portion and merging into the first stent, and a substantially straight lower segment extending from the arcuate anterior portion and merging into the first side of the bridge section; wherein the second support section comprises an arcuate anterior portion, a substantially straight upper segment extending from the arcuate anterior portion and merging into the first stent, and a substantially straight lower segment extending from the arcuate anterior portion and merging into the second side of the bridge section; wherein the bridge section symmetrically bridges the first and second support sections in a spaced apart lateral position and wherein the stents are spaced apart; wherein the stents have a posteriorly divergent lateral spacing; and wherein the bridge section is positioned distal to the anterior portions of the support sections.

14. The apparatus of any preceding or following embodiment: wherein each stent is connected to a corresponding support section; wherein each support section is connected to a corresponding side of the bridge section; and wherein each connection between a stent and a support section, and each connection between a support section and the bridge section, is an integrated seamless connection.

15. The apparatus of any preceding or following embodiment, wherein the apparatus comprises a flexible metal alloy material formed into the stents, support sections, and bridge section.

16. The apparatus of any preceding or following embodiment, wherein the metal alloy material comprises stainless steel, nickel-titanium or titanium-molybdenum.

17. The apparatus of any preceding or following embodiment, wherein at least a portion of the apparatus is covered with a biocompatible material.

18. The apparatus of any preceding or following embodiment, wherein the biocompatible material comprises a polymer.

19. The apparatus of any preceding or following embodiment, wherein the apparatus comprises a single resilient wire formed into the stents, support sections, and bridge section.

20. The apparatus of any preceding or following embodiment, wherein the apparatus comprises a biocompatible material formed into the stents, support sections, and bridge section.

21. The apparatus of any preceding or following embodiment, wherein the biocompatible material comprises a polymer.

22. The apparatus of any preceding or following embodiment, wherein each stent and associated support section in combination has a wing-like shape.

23. A nasal dilator apparatus, comprising: a first arcuate intranasal stent; a second arcuate intranasal stent; a first support section; a second support section; and an arcuate bridge section having a first side and a second side; wherein the first support section comprises an arcuate anterior portion, a substantially straight upper segment extending from the arcuate anterior portion and merging into the first stent, and a substantially straight lower segment extending from the arcuate anterior portion and merging into the first side of the bridge section; wherein the second support section comprises an arcuate anterior portion, a substantially straight upper segment extending from the arcuate anterior portion and merging into the first stent, and a substantially straight lower segment extending from the arcuate anterior portion and merging into the second side of the bridge section; wherein the bridge section symmetrically bridges the first and second support sections in a spaced apart lateral position and wherein the stents are spaced apart; wherein the stents have a posteriorly divergent lateral spacing; wherein the bridge section is positioned distal to the anterior portions of the support sections; and wherein stents, support sections, and bridge section are in combination a unitary structure.

24. The apparatus of any preceding or following embodiment: wherein the apparatus comprises a flexible metal alloy material formed into the stents, support sections, and bridge section; and wherein the metal alloy material is selected from the group consisting of stainless steel, nickel-titanium and titanium-molybdenum.

25. The apparatus of any preceding or following embodiment, wherein at least a portion of the apparatus is covered with a biocompatible polymer material.

26. The apparatus of any preceding or following embodiment, wherein the apparatus comprises a biocompatible polymer material formed into the stents, support sections, and bridge section.

As used herein, the singular terms "a," "an," and "the" may include plural referents unless the context clearly dictates otherwise. Reference to an object in the singular is not intended to mean "one and only one" unless explicitly so stated, but rather "one or more."

Phrasing constructs, such as "A, B and/or C", within the present disclosure describe where either A, B, or C can be present, or any combination of items A, B and C. Phrasing constructs indicating, such as "at least one of" followed by listing group of elements, indicates that at least one of these group elements is present, which includes any possible combination of these listed elements as applicable.

References in this specification referring to "an embodiment", "at least one embodiment" or similar embodiment wording indicates that a particular feature, structure, or characteristic described in connection with a described embodiment is included in at least one embodiment of the present disclosure. Thus, these various embodiment phrases are not necessarily all referring to the same embodiment, or to a specific embodiment which differs from all the other embodiments being described. The embodiment phrasing should be construed to mean that the particular features, structures, or characteristics of a given embodiment may be combined in any suitable manner in one or more embodiments of the disclosed apparatus, system or method.

As used herein, the term "set" refers to a collection of one or more objects. Thus, for example, a set of objects can include a single object or multiple objects.

As used herein, the terms "approximately", "approximate", "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to $\pm10\%$ of that numerical value, such as less than or equal to $\pm5\%$, less than or equal to $\pm4\%$, less than or equal to $\pm3\%$, less than or equal to $\pm2\%$, less than or equal to $\pm1\%$, less than or equal to $\pm0.5\%$, less than or equal to $\pm0.1\%$, or less than or equal to $\pm0.05\%$. For example, "substantially" aligned can refer to a range of angular variation of less than or equal to $\pm10°$, such as less than or equal to $\pm5°$, less than or equal to $\pm4°$, less than or equal to $\pm3°$, less than or equal to $\pm2°$, less than or equal to $\pm1°$, less than or equal to $\pm0.5°$, less than or equal to $\pm0.1°$, or less than or equal to $\pm0.05°$.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A nasal dilator apparatus, comprising:

first and second intranasal stents;

first and second support sections; and a bridge section;

wherein each support section comprises an arcuate anterior portion, a substantially straight upper segment extending from the arcuate anterior portion and merging into a corresponding stent, and a substantially straight lower segment extending from the arcuate anterior portion and merging into a corresponding side of the bridge section;

wherein the bridge section symmetrically bridges the first and second support sections in a spaced apart lateral position, wherein the stents are spaced apart, each stent comprising a semicircular curved portion that extends posteriorly in relation to the anterior portion of the corresponding support section, that curves upwardly from the corresponding substantially straight upper segment, and that then extends anteriorly and curves toward the substantially straight upper segment to terminate at a distal end that is spaced apart from the substantially straight upper segment, such that the stent can extend in a posterosuperior direction and approximately follow the curve of the inferior edge of the piriform aperture of a nose; and wherein the bridge section is positioned distal to the anterior portions of the support sections.

2. The apparatus of claim 1:

wherein the stents are spaced apart and develop from the first and second support sections along two adjustably inclined planes forming a flare;

the stents having each an adjustable curvature and being each arranged to apply gentle pressure to open the nasal passage without applying pressure to the lesser alar cartilage.

3. The apparatus of claim 2, wherein the adjustable curvature comprises a radius of curvature adjustable from about 4 mm to about 7.5 mm.

4. The apparatus of claim 1, wherein the apparatus comprises a flexible metal alloy material.

5. The apparatus of claim 4, wherein the metal alloy material comprises stainless steel, nickel-titanium or titanium-molybdenum.

6. The apparatus of claim 1, wherein at least a portion of the apparatus is covered with a biocompatible material.

7. The apparatus of claim 6, wherein the biocompatible material comprises a polymer.

8. The apparatus of claim 1, wherein the apparatus comprises a single resilient wire formed into the stents, support sections, and bridge section.

9. The apparatus of claim 1, wherein the apparatus comprises a biocompatible material formed into the stents, support sections, and bridge section.

10. The apparatus of claim 9, wherein the biocompatible material comprises a polymer.

11. The apparatus of claim 1, wherein each stent and associated support section in combination has a wing-like shape.

12. The apparatus of claim 1, wherein the stents have a posteriorly divergent lateral spacing.

13. The apparatus of claim 1:

wherein said stents, said support sections, and said bridge section are in combination a unitary structure.

14. The apparatus of claim 13:

wherein the apparatus comprises a flexible metal alloy material formed into the stents, support sections, and bridge section; and wherein the metal alloy material is selected from the group consisting of stainless steel, nickel-titanium and titanium-molybdenum.

15. The apparatus of claim 14, wherein at least a portion of the apparatus is covered with a biocompatible polymer material.

16. The apparatus of claim 13, wherein the apparatus comprises a biocompatible polymer material formed into the stents, support sections, and bridge section.

* * * * *